United States Patent
Chou et al.

(10) Patent No.: US 10,772,535 B2
(45) Date of Patent: Sep. 15, 2020

(54) SELF-DIAGNOSTIC METHOD FOR JAUNDICE AND AN APP PRODUCT THEREBY

(71) Applicants: Hsin-Hsu Chou, Chiayi (TW); Yuh-Hwan Liu, Tainan (TW)

(72) Inventors: Hsin-Hsu Chou, Chiayi (TW); Yuh-Hwan Liu, Tainan (TW)

( * ) Notice: Subject to any disclaimer, the term of this patent is extended or adjusted under 35 U.S.C. 154(b) by 1008 days.

(21) Appl. No.: 13/974,018

(22) Filed: Aug. 22, 2013

(65) Prior Publication Data

US 2015/0057551 A1   Feb. 26, 2015

(51) Int. Cl.
| | | |
|---|---|---|
| A61B 5/02 | (2006.01) | |
| A61B 5/103 | (2006.01) | |
| A61B 5/00 | (2006.01) | |
| G06T 7/00 | (2017.01) | |

(52) U.S. Cl.
CPC .......... *A61B 5/1032* (2013.01); *A61B 5/0077* (2013.01); *A61B 5/441* (2013.01); *A61B 5/6898* (2013.01); *A61B 2503/045* (2013.01); *A61B 2560/0233* (2013.01); *A61B 2576/02* (2013.01); *G06T 7/0012* (2013.01)

(58) Field of Classification Search
CPC ............ A61N 5/0621; A61B 2503/045; A61B 5/441; G06T 7/0012
See application file for complete search history.

(56) References Cited

U.S. PATENT DOCUMENTS

| | | | | |
|---|---|---|---|---|
| 2007/0154095 A1* | 7/2007 | Cao | ..................... | G06K 9/00234 382/190 |
| 2008/0008370 A1* | 1/2008 | Chio | ...................... | A61B 5/441 382/128 |
| 2009/0245603 A1* | 10/2009 | Koruga | .................. | A45D 44/00 382/128 |
| 2011/0119075 A1* | 5/2011 | Dhoble | ................. | G06F 19/322 705/2 |
| 2014/0323832 A1* | 10/2014 | Thangaraj | .......... | A61B 5/14546 600/315 |

OTHER PUBLICATIONS

Mansor, Jaundice in Newborn Monitoring using Color Detection Method, Feb. 2012, pp. 1631-1635.*
Clikjaundice, Diagnosing Jaundice by Phone: How ClikJaundice is using mobile technology to empower parents at the BoP, Jun. 2013.*

* cited by examiner

*Primary Examiner* — Puya Agahi
(74) *Attorney, Agent, or Firm* — Maschoff Brennan

(57) ABSTRACT

A self-diagnostic method for momentarily generating a jaundice index, clinically equivalent to the serum bilirubin level, for newborns including Step S1: obtaining a newborn's image of face based on color markers; Step S2: color correction of the image based on the color markers; Step S3: calculating jaundice index based on color information of pixels of the facial image, excluding undesired interfering. The method can be executed by an APP (Application) product.

12 Claims, 5 Drawing Sheets

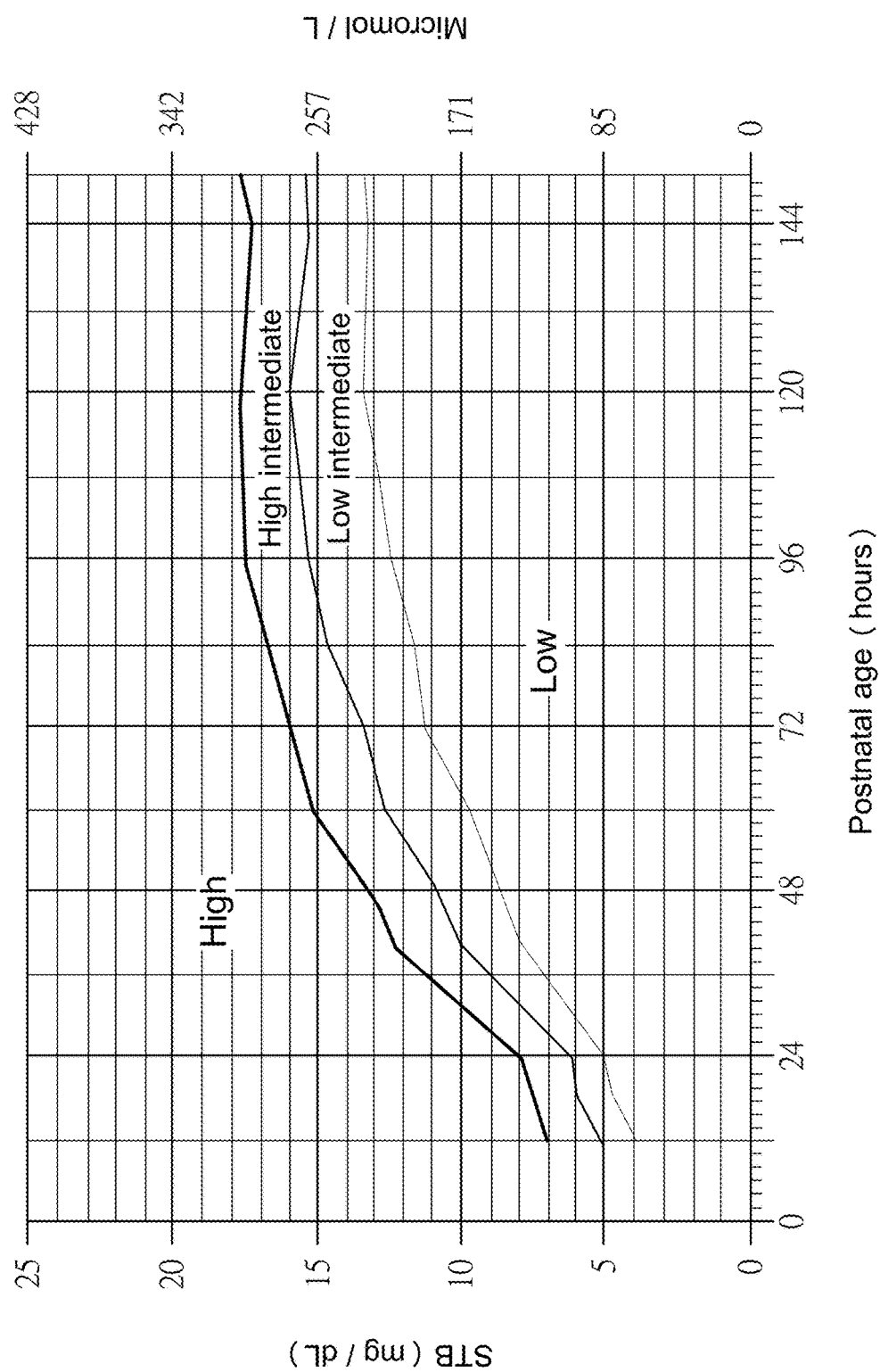
F I G. 5

SELF-DIAGNOSTIC METHOD FOR JAUNDICE AND AN APP PRODUCT THEREBY

BACKGROUND OF THE INVENTION

1. Field of the Invention

This invention relates to a method for diagnosing jaundice of the newborn, particularly an improved method for accurately identifying a newborn's jaundice in a self-regulating manner, and a product of application software (APP) thereby.

2. Description of the Related Art

The serum bilirubin level is one of the blood tests commonly applied to the newborn, which is also an important focus closely observed by medical staffs and the newborn's parents. Newborn jaundice occurs when a baby has a high level of bilirubin in the blood, which may cause kernicterus and endanger the baby's brain, resulting in cerebral palsy, deafness, mental retardation and other side effects.

Currently jaundice detection methods rely mainly on small amount of blood for testing. However, this procedure is in nature invasive and may cause pain, bleeding, wound infection and other side effects, resulting in limited application in actual practice as well as some concerns for patients. Therefore, blood tests for jaundice are often applied only after family members or health care workers have observed symptoms of jaundice in the baby's skin. However, the naked eyes are merely subjective judgments, which are especially true for new parents lacking professional training and experience, who often misjudge the situation and cause unrecoverable delay or unnecessary blood tests in treating jaundice.

Jaundice meters works by emitting a light beam to the baby's skin and analyzing wavelengths of light reflected back to provide a non-invasive numerical evaluation of jaundice. However jaundice meters are expensive and may not be afforded by an ordinary family. Also jaundice meters are limited in practice to most newborn infants of one to two month-old, not convenient to the public in general.

SUMMARY OF THE INVENTION

It is the goal of this invention to provide an objective diagnostic tool of the newborn's serum bilirubin level by means of non-invasive image processing using the currently popular camera-included smartphones, tablets or PC's to facilitate momentary self-diagnosis for the newborn's parents and thereby reacts in time to a newborn's serum bilirubin level when higher than normal. Namely, the instant invention reduces the waste in efforts and medical resources for unnecessary blood tests.

The procedures included in the self-diagnostic method for jaundice are chronologically ordered steps, as described below:

Step 1, i.e. S1: placing a plurality of color markers aside a newborn to obtain a self-diagnostic image including an image of the newborn's face and an image of the plurality of color markers;

Step 2, i.e. S2: correcting colors of the image of the newborn's face in S1 based on the image of the plurality of color markers; and Step 3, i.e. S3: obtaining the index of jaundice of a color normalized image of the newborn's face based on color information of the color normalized image of the newborn's face with undesirable images eliminated.

In S1, the image of the newborn's face and color markers are obtained with smart phones, tablets or personal computers by way of a camera and an APP programming electronic means implementing step-by-step procedures disclosed in the present invention. The color markers include three different colors, a pure red, a pure green, and a pure blue. To facilitate a clear image when photographing, it is preferrably that some outlines are proposed for locations of color markers.

The birth time of the newborn is (either before or after taking the image) also taken into account in reference to the normal range of a newborn jaundice of the same postnatal age. Preferably, color markers are arranged around the baby's face in the image view in the shape one or more rectangles. To avoid undesired interference effecting the image analysis, it is preferrably that objects surrounding the newborn do not contain too much of the colors of red, green, blue, and yellow.

In step S2, a color correction or revision is made to the whole image taken. Particular, the RGB color model is adopted in performing step S2. The normalization is applied to the whole color image based on the average color value of the color markers obtained from the color image taken in step S1. At an initial stage of step S2, i.e. S21, color markers are first automatically grabbed, followed by obtaining the image pixel number denoted as Nx within the area of color markers, with $x \in \{r, g, b\}$, namely, x representing red, green or blue color, and therefore Nx representing an image pixel number of the pure red color marker, an image pixel number of the pure green color marker and an image pixel number of the pure blue within the geometric area (for instance, a rectangle) defined by color markers. When the image pixel number Nx within the area of color markers are all larger than a threshold value, an average color value of the pure red color marker, an average color value of the pure green color marker and an average color value of the pure blue color marker are obtained. After the average color value of the pure red color marker, the average color value of the pure green color marker and the average color value of the pure blue color marker are obtained, step S2 follows, which performs (color) normalization of the whole image taken in step S1, based on the average color value of the pure red color marker, the average color value of the pure green color marker and the average color value of the pure blue color marker. In particular, in step S21, areas containing pixels of colors very similar to pure red, pure green and pure blue are respectively grabbed and connected respectively as the largest continuous area for color markers of red, green, and blue, respectively. $P_r$ is defined as an average value of the red channel in the color marker of red, $P_g$ is defined as an average value of the green channel in the color marker of green, and $P_b$ is defined as an average value of the blue channel in the color marker of blue.

In step S22, color normalization is performed to the image based on the average color value of the pure red color marker, the average color value of the pure green color marker and the average color value of the pure blue color marker. In particular, each image pixel is readjusted in reference to the color information of the red, green and blue channel, respectively for eliminating errors in the color analysis for obtaining an index for jaundice.

In the step S3, the color information of the facial image pixels are obtained from the HSV (Hue Saturation Value) color model to obtain the jaundice index. In the initial step of S3, facial skin pixels are screened according to the range of skin hues based on the HSV color model, and the number of which are totaled as $N_{sk}$. Jaundice pixels are further grabbed among the facial skin pixels based on the range of hue of jaundice. The average value of saturation of jaundice pixels, and the Jaundice Skin Ratio (JSR) are then obtained. Finally, the average values of saturation of jaundice pixels are converted by specific functions to a jaundice index, medically equivalent to the jaundice index obtained from blood tests.

In step S31, facial skin pixels are screened according to the range of statistic newborn facial skin hues, and the number of which are totaled as $N_{Sk}$, i.e. the total number of facial skin pixels $N_{Sk}$. Let $N_E$ represent the total number of image pixels within the elliptical facial outline (2), $S_E$ be the average saturation $S_E$, and SER be the ratio of $N_{Sk}$, the Skin Ellipse ratio, between $N_{Sk}$ and $N_E$, as shown below:

$$SER = N_{Sk}/N_E.$$

In step S32, jaundice pixels are further grabbed among these facial skin pixels based on the statistic range of hues of the newborn jaundice. In step S33, the average saturation of jaundice pixels, and the Jaundice Skin Ratio (JSR) are obtained. In step S34, the average saturation value of jaundice pixels is converted to a jaundice index.

The step S34 includes conversion of the average saturation of jaundice pixels to a jaundice index, which is medically equivalent to the serum bilirubin level obtained from blood tests. Furthermore, a further required diagnostics is issued and/or a doctor visit is suggested when the generated jaundice index is above average risk of stroke.

The method disclosed can be implemented as an APP product, downloaded from internet or other equivalent channels to smart phones, tablets, PC's and other similar electronics. The color analysis disclosed in the application is conveniently made in accordance with color markers in real-time. When the facial skin pixel number is not larger than a quality threshold value (due to dim lights, or unfavorable locations of color markers), the user would be requested for retaking an image. The output of the jaundice index is also converted to its medical equivalent from blood tests, scientifically more accurate than visual estimates for not missing out the timing of treatment when necessary.

BRIEF DESCRIPTION OF THE DRAWINGS

FIG. 5: A chart of STB vs. postnatal age published by American Academy of Pediatrics

DETAILED DESCRIPTION OF THE PREFERRED EMBODIMENTS

Figure 1:
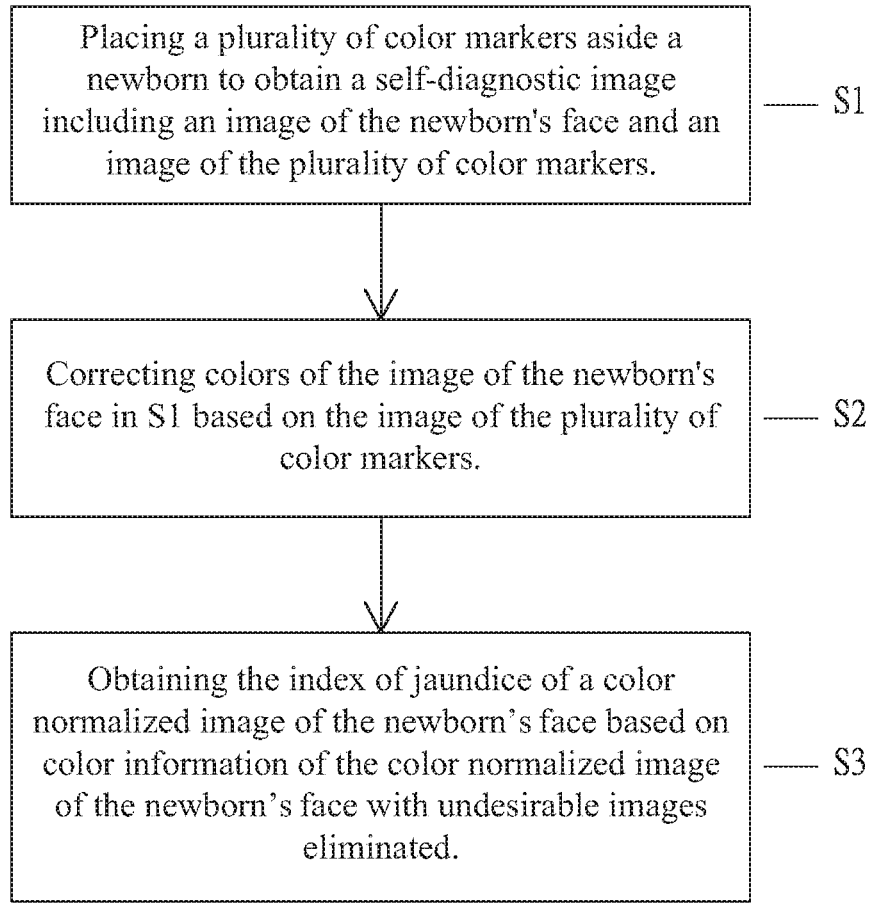
FIG. 1 shows the steps of the method of the instant invention o
Figure 2:
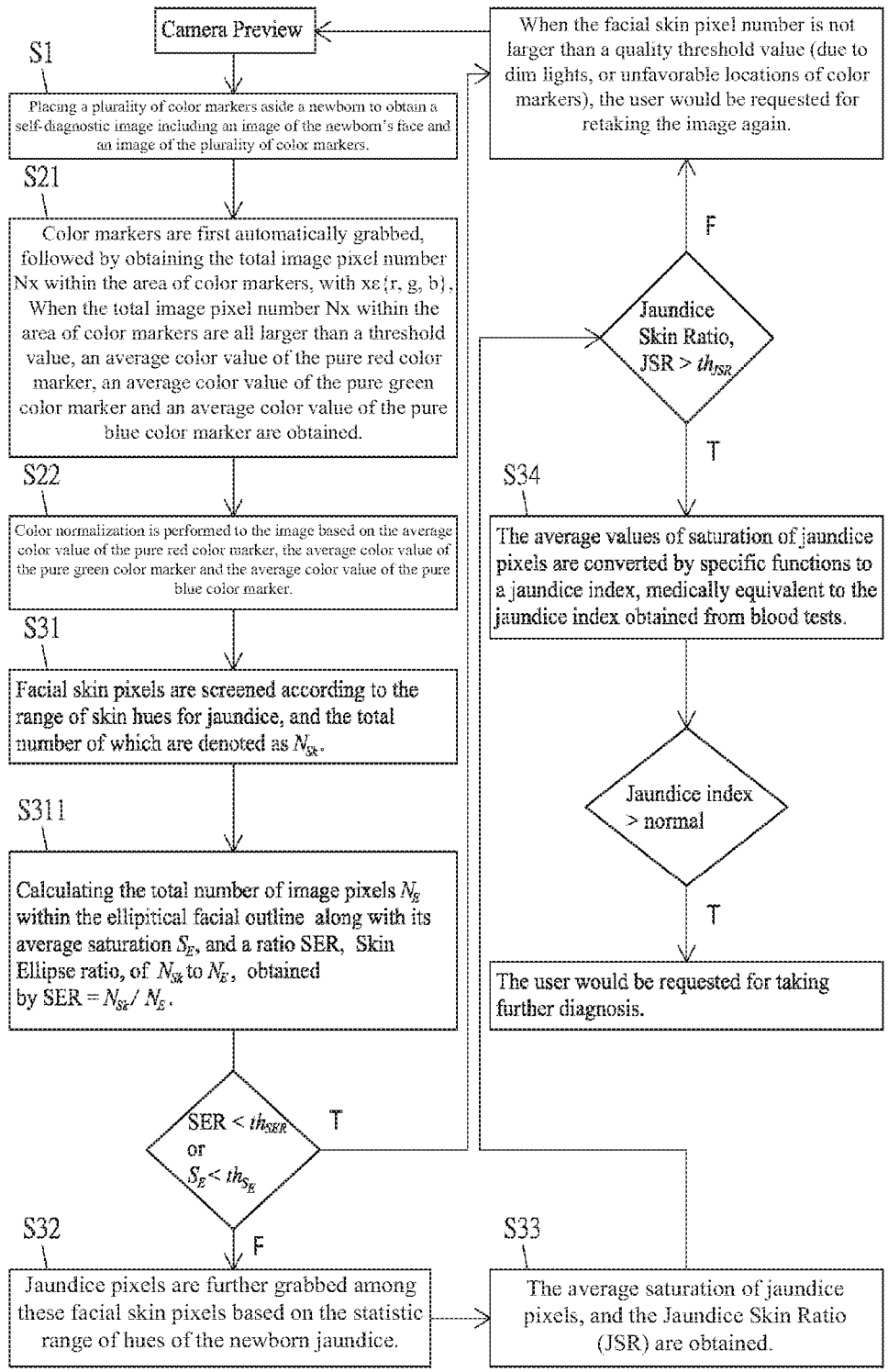
FIG. 2 shows the flowchart of the method of the instant invention.
Figure 3:
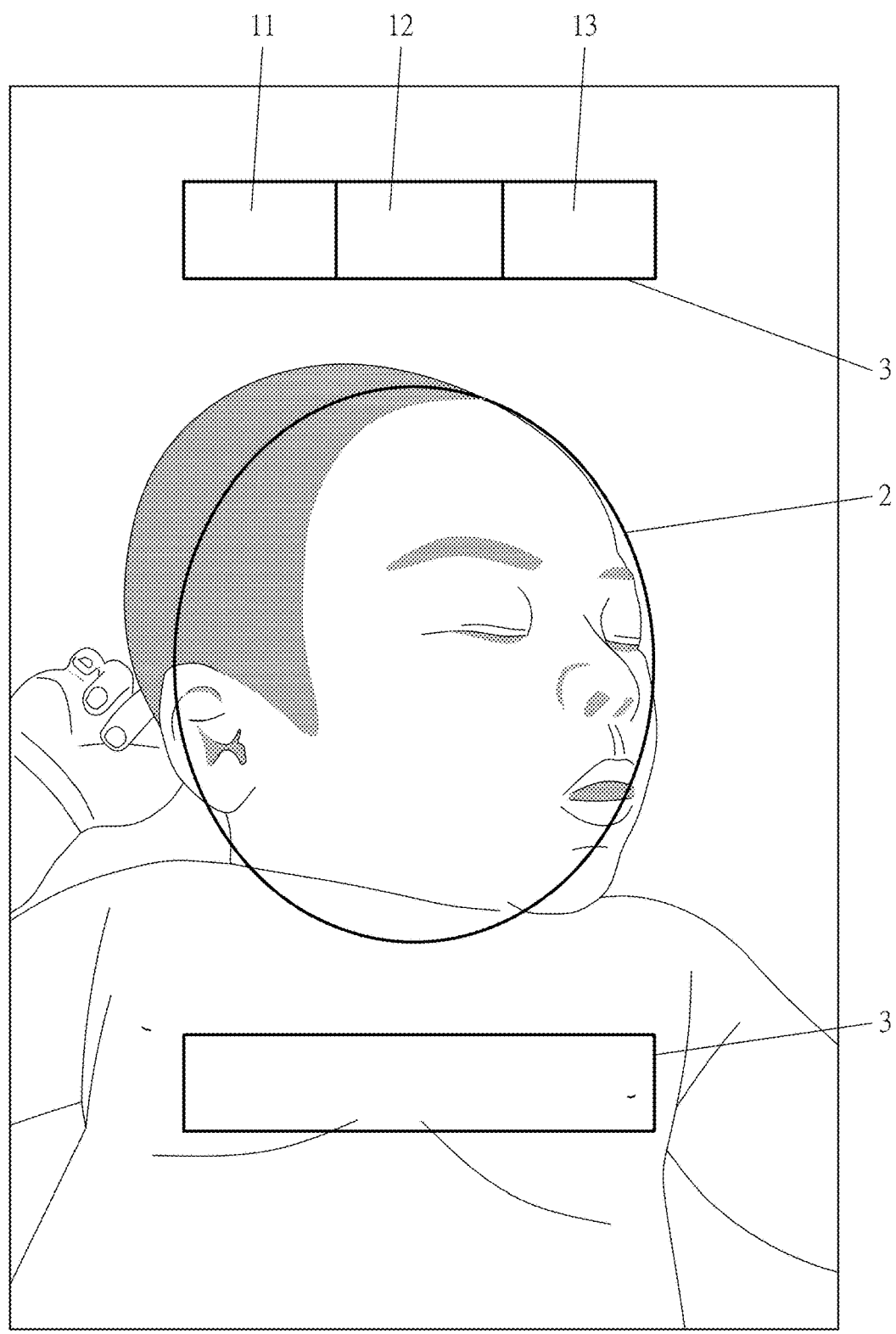
FIG. 3 shows image taken as well as the color markers in the image.

Please refer first to FIG. 1-3. FIG. 1 shows the procedural steps of the present application. FIG. 2 is the flow chart of the method disclosed in the present application. FIG. 3 shows the color markers applied in the image taken in the instant application. In step S1, newborns face and color markers are photographed; in step S2, color correction; in step S3, calculation is made to obtain the index for jaundice based on color information of the color normalized image of the newborn's face obtained in step S2 in the newborn facial image taken in the step S1, excluding undesired image pixels.

Wherein in step S1, smart phones, tablets or PC's with a camera or photographing function are used for taking a newborn's facial image, including the color markers thereof as defined in the instant method. The color markers contain the pure red marker No. 11, the pure green marker No. 12, and the pure blue marker No. 13, each marker of size greater than 1 cm². As shown in FIG. 3, in the preview for taking an image using an electronic mean (such as smart phones, tablets or personal computers, etc.), the elliptical facial outline (2) of a newborn is pre-set in the shape of an ellipse, and the two rectangles are allocated as the two different preferred locations for color markers of pure red (11), pure green (12) and pure blue (13). In the preferred embodiment of the instant invention, the preferred location for color markers 11, 12, and 13 is in the upper location of the preview for an image. Also, the birth date and time of the newborn is taken into account as a factor of postnatal age to improve accuracy in the reading of the index of the newborn's jaundice, either before or after taking the image photo. The input data of birth date and time of the newborn is applied in reference to FIG. 5, which shows serum total bilirubin level, or STB, (in mg/dL) vs. postnatal age (in hours). Background colors within the preview are, preferably, so arranged to avoid objects surrounding the newborn, such as wrapping clothes, mattresses or pillows, to contain the colors of red, green, blue, and even yellow to reduce interference with the later color analysis of the image taken.

In step S2, color correction is performed on the image taken, based on the conventional RGB color model. Normalization of color pixels of the image taken are performed according to the average color values of color markers. To be more specific, at an initial stage of step S2, i.e. S21, color markers are first automatically grabbed, followed by obtaining the image pixel number Nx within the area of each of the three color markers, with $x\varepsilon\{r, g, b\}$, namely, x representing red, green or blue color, and therefore Nx representing an image pixel number of the pure red color marker, an image pixel number of the pure green color marker and an image pixel number of the pure blue within the geometric area (for instance, a rectangle) defined by color markers. When the image pixel number Nx within the area of color markers are all larger than a threshold value, an average color value of the pure red color marker, an average color value of the pure green color marker and an average color value of the pure blue color marker are obtained. After the average color value of the pure red color marker, the average color value of the pure green color marker and the average color value of the pure blue color marker are obtained, step S22 follows, which performs (color) normalization to the photo image taken, based on the average color value of the pure red color marker, the average color value of the pure green color marker and the average color value of the pure blue color marker. In step S21, after the photo image of a newborn is taken, areas containing colors closer to pure red, pure green, and pure blue are respectively grabbed within the (for instance, rectangular) area of the two color marker contours (3). Afterwards, the pure red color marker (11), pure green color marker (12), and pure blue color marker (13) are then defined to be the largest continuous area connecting the areas of colors closer to pure red, pure green, and pure blue, respectively.

In mathematical terms, to automatically grab color markers, mxRri, mxRgi, mxRbi are defined to be the largest continuous area for Rri, Rgi, Rbi, respectively. Whereas, maxi {mxRri, mxRgi, mxRbi} is defined to be a color area within the ith rectangular area that contains the maximum mxRri, mxRgi, mxRbi, corresponding to pure red marker (11), pure green marker (12) and pure blue marker (13), respectively.

In an example embodiment of the instant application, color markers of pure red (11), pure green (12) and pure blue (13) can be grabbed within the color marker contour (3) above the newborn's face. The total number of color pixels within each of the mxRri, mxRgi, mxRbi is defined as Nx, with x∈{r,g,b}. When Nx is less than a preset threshold value of $th_{Nx}$, it implies that either color markers are not correctly grabbed within the specified color marker contour (3), or the light is too dim for a clear photo image to be taken. Nx is preset to correspond to the image resolution of the camera: a higher value of Nx corresponds to a higher image resolution. For instance, for an image resolution of 4752×3168, $th_{Nx}$ is recommended to be 10,000. When $th_{Nx}$ is less than 10,000, it is recommended that the locations for color markers be readjusted for retaking a better image.

{$CP_i$} is set to be the collection of the image pixels within the specified color marker contour (3), wherein i∈{0,1}, and i does not belong to a specific area. Let $Rr_i$, $Rg_i$, $Rb_i$ be the area of a color closet to pure red, pure green and pure blue, respectively, within the ith rectangular area, x∈{r, g, b}, $Rx_i=\{P\}, P\in\{CP_i\}$, and $|(P_r,P_g,P_b)-(x_r,x_g,x_b)|<th\_p$, wherein x∈{r, g, b},
$(r_r,r_g,r_b)=(255,0,0)$,
$(g_r,g_g,g_b)=(0,255,0)$,
$(b_r,b_g,b_b)=(0,0,255)$,
|a−b| is the distance between a and b
$\sqrt{(a_r-b_r)^2+(a_g-b_g)^2+(a_b-b_b)^2}$ th_cp represents the preset threshold value for the color markers, preferably set as 10.

$P_r$ is defined to be the average value of the red channel in the red marker (11). In the same manner, $P_g$ is defined to be the average value of the green channel in the green marker (12), and $P_b$ is defined to be the average value of the blue channel in the blue marker (11).

There are two rectangular color marker contours (3) shown in FIG. 5. In actual practice, one single color marker contour would do. If color markers for some unavoidable reasons cannot be physically grabbed within the specified color marker contour (3) when the photo image is being taken, color markers can temporarily randomly be placed outside of the facial image within the view of the image taken. After the image is taken, color markers can be manually regrabbed by choosing a central point of a color marker followed by automatic regrab as previously described for the instant application.

In step S22, color normalization is performed to the whole image based on the average color value of the pure red color marker, the average color value of the pure green color marker and the average color value of the pure blue color marker. In particular, each image pixel is readjusted correspondingly to the red, green and blue channel, respectively such that the red channel of the red marker (11) is closer to 255, which is also true of the green channel of the green marker (12), as well as the blue channel of the blue marker (13).

Let normalization factor $$f_r = \frac{255}{P_r}, f_g = \frac{255}{P_g}, f_b = \frac{255}{P_b},$$

such that the red channel $C_r$ of each image pixel adjusted in normalization as $C'_r=f_r\times C_r$, in the same manner, the green channel $C_g$ of each image pixel adjusted n normalization as $C'_g=f_g\times C_g$, and the blue channel $C_b$ of each image pixel adjusted n normalization as $C'_b=f_b\times C_b$ Error in RGB color analysis of the image can be reduced by calculation of pixel value of each image pixel corresponding to the red, green and blue marker (11, 12, and 13).

Figure 4:
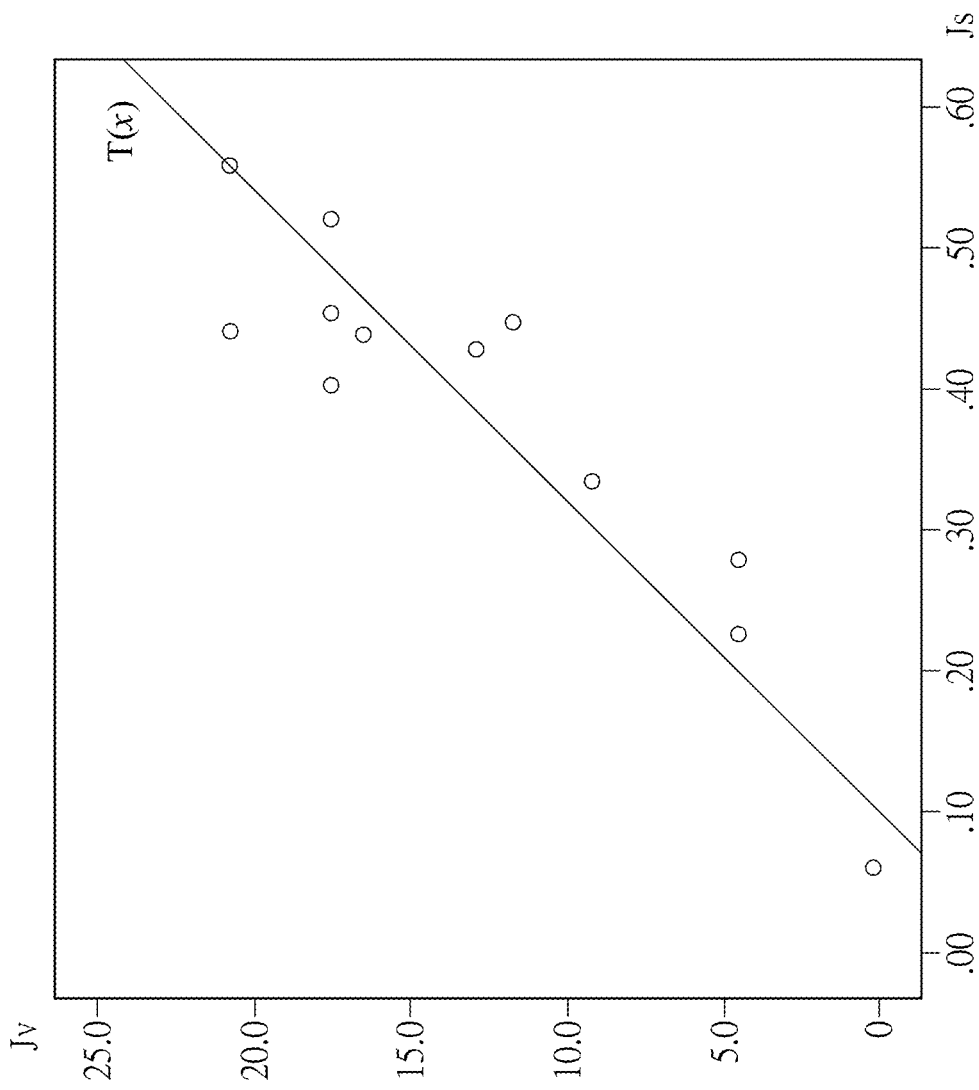
FIG. 4: A regression statistic chart of average values of saturation vs. bilirubin levels of the instant invention.

Refer to FIG. 4, which shows the regression chart of average saturation vs. serum bilirubin level of the present invention. In step S3, the color information of the facial image pixels obtained for calculating the jaundice index is based on an HSV (Hue Saturation Value) color model. Color information of facial skin pixels are automatically obtained, and further screened for areas of jaundice. The saturation average of pixels in the areas of jaundice is first obtained, and then converted by a specific function to a jaundice index, equivalent in medical terms to the serum bilirubin level obtained in blood tests. The evaluation of the sampling quality of the image taken is based on the ratio between the jaundice pixels and the facial skin pixels, or Jaundice Skin Ratio, (JSR). The sampling quality of the image taken is less desired when JSR is less than the preset threshold value $th_{JSR}$, implying a larger error in the calculation of the jaundice index. $th_{JSR}$ is a preset threshold value statistically obtained by the instant invention.

In the initial step of S3, S31, facial skin pixels are screened according to the range of skin hues for jaundice, and the total number of which are denoted as $N_{Sk}$. In step S32, jaundice pixels are then grabbed among these facial skin pixels based on the range of hues of jaundice. In step S33, the average value of saturation of jaundice pixels, and the Jaundice Skin Ratio (JSR) are calculated. In step S34, the average value of saturation of jaundice pixels is converted to a jaundice index.

$C'_r, C'_g, C'_b$ (RGB) is conventionally converted to HSV by $$M = \max(R, G, B) \qquad (1)$$
$$m = \min(R, G, B)$$
$$C = M - m$$

$$H' = \begin{cases} \text{undefined}, & \text{if } C = 0 \\ \frac{G-B}{C}, & \text{if } M = R \\ \frac{B-R}{C}+2, & \text{if } M = G \\ \frac{R-G}{C}+4, & \text{if } M = B \end{cases}$$

$$H = 60° \times H'$$

$$V = \frac{1}{3}(R+G+B) \qquad (2)$$

$$S = \begin{cases} 0, & \text{if } C = 0 \\ \frac{c}{v}, & \text{otherwise} \end{cases} \qquad (3)$$

In step S31, the color information of RGB is converted to that of HSV, the range of hues in facial skin of a newborn is set as a parameter (about 42.5±18.5 in the preferred embodiment of the invention). The collection of the facial skin pixels inside the elliptical facial outline (2) of the image taken are denoted as Sk.

In step S31, if the facial skin is unable to fit completely into the elliptical facial outline (2), after an image is taken, a user can manually adjust the elliptical facial outline (2) in size, location, and angles, such that the facial skin can be recaptured in the manually adjusted elliptical facial outline (2).

To improve the quality in sampling of the image pixels, in step S311, the total number of image pixels $N_E$ within the elliptical facial outline (2), its average saturation $S_E$, and the ratio SER, i.e. the ratio between $N_{Sk}$ (i.e. the total number of facial skin pixels) and $N_E$ (i.e. the total number of pixels within the elliptical facial outline 2) are all obtained $$SER = \frac{N_{Sk}}{N_E}.$$

When SER<$th_{SER}$, the quality of the image taken is evaluated as poor and recommended to retake the image.

In the instant invention, when SER<$th_{SER}$ (70%), the sampling quality of the image taken is evaluated as poor and recommended to have the image retaken.

The average value of saturation of all image pixels within the elliptical facial outline (2) is denoted as $S_E$. In the instant invention, when $S_E$<$th_{SER}$ (0.5), the light source is deemed insufficient to produce a fair sampling and is recommended to have the image retaken.

In step S32, the range of hues for newborns is statistically set as a parameter for jaundice pixels, which is about 40-60 in the instant invention. The collection of jaundice pixels obtained among the facial pixels of the image is denoted as J.

The collection of jaundice pixels (or pixels in a jaundice area) is denoted as J, with the total number of J denoted as $N_J$. The collection of facial skin pixels in the image taken is denoted as Sk, with the total number of Sk denoted as $N_{Sk}$. JSR is defined as the ratio between $N_J$ and $N_{Sk}$.

To avoid misjudgment due to poor quality of the image, the image is evaluated as poor when JSR is less than $th_{JSR}$ (50%), and hence retaking of the image is recommended to avoid an error in $J_s$.

Average saturation of J is denoted as $J_s$, which is converted by a specific function T(x) to a jaundice index, clinically equivalent to the serum bilirubin level obtained from blood tests. As shown in FIG. 4, the function T(x) is a regressional statistic function of $J_s$ and $J_v$, both of which are positively correlated. A higher value of $J_s$ corresponds to a higher value of $J_v$, and vice versa. FIG. 5 shows a chart of STB vs. postnatal age published by American Academy of Pediatrics for as a guideline for treatment.

The procedural steps in the method can be implemented by APP (Application software), downloaded from the internet to smart phones, tablets, etc.

The color analysis is conveniently made in accordance with color markers in real-time. When the facial skin pixel number is not larger than a quality threshold value (due to dim lights, or unfavorable locations of color markers), the user would be requested for retaking an image to avoid errors in producing a biased jaundice index.

The invention claimed is:

1. A non-transitory computer-readable storage medium encoded with executable instructions for execution by a processor to detect jaundice by a self-diagnostic method for jaundice, including:
   Step S1: placing a plurality of color markers aside a newborn to obtain a self-diagnostic image including an image of the newborn's face and an image of the plurality of color markers, wherein the self-diagnostic image is taken by a smart phone, tablet, or personal computer with a camera equipped with the executable instructions, and the color markers include a pure red color marker, a pure green color marker and a pure blue color marker;
   Step S2: color correction of the image of a newborn's face based on the image of the plurality of color markers, wherein step S2 includes;
   Step S21 automatically grabbing the color markers using a RGB (Red, Green, and Blue) color model so as to obtain a pixel array of the grabbed color markers, the pixel array having three array elements including a red color element, a green color element and a blue color element,
   and obtaining an image pixel number of each obtained array element such that an image pixel number of the pure red color marker, an image pixel number of the pure green color marker and an image pixel number of the pure blue color marker are obtained, and then when the image pixel number of the pure red color marker, the image pixel number of the pure green color marker and the image pixel number of the pure blue color marker are all larger than a threshold value, obtaining an average color value of the pure red color marker, an average color value of the pure green color marker and an average color value of the pure blue color marker,
   Step S22 color normalization of the image of the newborn's face by using the average color value of the pure red color marker, the average color value of the pure green color marker and the average color value of the pure blue color marker, and
   Step S3: obtaining a jaundice index of a color normalized image of the newborn's face based on color information of the color normalized image of the newborn's face, wherein step S3 includes:
   Step S31 grabbing facial skin pixels based on ordinary hues of skin and obtaining the total number of the grabbed facial skin pixels,
      wherein if the facial skin pixel number is not larger than a quality threshold value, then return to grab the image again,
   and
      wherein if the
   facial skin pixel number is larger than the quality threshold value, then continues to step S32,
   Step S32 grabbing jaundice pixels among the facial skin pixels based on a statistic range of hues of jaundice,
   Step S33 obtaining an average saturation of the jaundice pixels from the grabbed jaundice pixels such that the number of jaundice pixels is obtained, and obtaining a Jaundice Skin Ratio (JSR) which is a ratio of a number of jaundice pixels to a number of facial skin pixels;
      wherein when JSR is less than a preset value, then return to grab the image again, and
      when the JSR is equal to or larger than the preset value, the method then continues to step S34, Step S34 converting the average saturation value of jaundice pixels to a jaundice index,
wherein when the jaundice index is larger than a preset value of a normal jaundice index, an indication that a further diagnostics is required is issued.

2. A self-diagnostic method for jaundice as claimed in claim 1, wherein objects around the newborn which contain colors of red, green, blue or yellow are avoided.

3. A self-diagnostic method for jaundice as claimed in claim 1, wherein a preview of the image includes a facial outline and one or more color marker contour, with Step S21 includes automatic grabbing the color markers and allocating the color markers within the color marker contour, for the color marker of red: grabbing and connecting the facial skin pixels within the one or more contour of a distance to a pure red pixel greater than a red threshold as the largest continuous area thereof, and defining a pure red marker (11) therein;

for the color marker of green: grabbing and connecting the facial skin pixels within the one or more contour of a distance to a pure green pixel greater than a green threshold as the largest continuous area thereof, and defining a pure green marker (12) therein; and for the color marker of blue: grabbing and connecting the facial skin pixels within the one or more marker contour of a distance to a pure blue pixel greater than a blue threshold as the largest continuous area thereof, and defining a pure blue marker (13) therein;

the pure red pixel $(r_r, r_g, r_b)=(255, 0, 0)$,
the pure green pixel $(g_r, g_g, g_b)=(0, 255, 0)$,
the pure blue $(b_r, b_g, b_b)=(0, 0, 255)$ Step S22 includes color normalization to each of the pixels in the image in reference to the red channel, the green channel and the blue channel, respectively, such that the value of the red channel, the green channel and the blue channel is inversely proportionally to an average value of a red channel in the red color marker, an average value of a green channel in the green marker and an average of a blue channel in a blue marker, and adjusted to a number.

4. A self-diagnostic method for jaundice as claimed in claim 3, wherein in the Step S31, RGB color information is converted to HSV (Hue, Saturation and Value) color information, in reference to a statistical range of hues in facial skin of newborns, facial skin pixels within the ellipitical facial contour are denoted as $S_k$, with a total number of $S_k$ denoted as $N_{sk}$;

Step S33 includes obtaining jaundice pixels J among the facial skin pixels $S_k$, with the total number of J denoted as $N_J$, with the total number of $S_k$ denoted as $N_{sk}$, wherein the image is evaluated as poor when the ratio between $N_J$ and $N_{sk}$ is less than $th_{JSR}$ (50%), and retaking of the image is recommended;

Step S34 includes first obtaining a saturation average $l_s$ of jaundice pixels, then converting by a function $T(x)$ to a jaundice index, clinically equivalent to the serum bilirubin level lv from blood tests, wherein the function $T(x)$ is a regressional statistic function of Js and Jv.

5. A self-diagnostic method for jaundice as claimed in claim 4, wherein the Step S3 further includes calculating the total number of image pixels $N_E$ within the elliptical facial outline along with its average saturation $S_E$, and a ratio SER, Skin Ellipse ratio of $N_{sk}$ to $N_E$ obtained by $SER=N_{sk}/N_E$ when $SER<th_{JSR}$, the quality of the image taken is evaluated as poor and recommended to retake the image;
when $SER>th_{JSR}$, and $S_E>th_{SE}$, proceed to Step S32.

6. A self-diagnostic method for jaundice as claimed in claim 1, wherein the birth time of the newborn is taken into account, together with the calculation of the jaundice index, to evaluate the need for a doctor visit or photo therapy.

7. A self-diagnostic method for jaundice as claimed in claim 1, executable in an Application software downloadable to electronic means.

8. A self-diagnostic method for jaundice as claimed in claim 2, executable in an Application software downloadable to electronic means.

9. A self-diagnostic method for jaundice as claimed in claim 3, executable in an Application software downloadable to electronic means.

10. A self-diagnostic method for jaundice as claimed in claim 4, executable in an Application software downloadable to electronic means.

11. A self-diagnostic method for jaundice as claimed in claim 5, executable in an Application software downloadable to electronic means.

12. A self-diagnostic method for jaundice as claimed in claim 6, executable in an Application software downloadable to electronic means.

* * * * *